United States Patent [19]

Yin et al.

[11] Patent Number: 4,935,359
[45] Date of Patent: Jun. 19, 1990

[54] FERMENTATION PROCESS

[75] Inventors: Guanglin Yin; Zengxin Tao; Zizheng Yan; Wenzhu Ning; Changhui Wang; Shuiding Wang, all of Beijing, China

[73] Assignee: Institute of Microbiology, Beijing, China

[21] Appl. No.: 146,276

[22] Filed: Feb. 3, 1988

[30] Foreign Application Priority Data

Feb. 7, 1987 [CN] China ............................ 87100547
Mar. 23, 1987 [EP] European Pat. Off. ........ 87810169.0

[51] Int. Cl.$^5$ .......................... C12P 7/60; C12N 1/20; C12R 1/01; C12R 1/11
[52] U.S. Cl. ................................ 435/138; 435/252.1; 435/822; 435/837
[58] Field of Search ............... 435/138, 837, 822, 253, 435/252.1

[56] References Cited

U.S. PATENT DOCUMENTS

| | | | |
|---|---|---|---|
| 3,922,194 | 11/1975 | Sonoyama et al. | 435/837 |
| 3,963,574 | 6/1976 | Sonoyama et al. | 435/138 |
| 3,998,697 | 12/1976 | Sonoyama et al. | 435/138 |

FOREIGN PATENT DOCUMENTS

| | | |
|---|---|---|
| 0213591 | 3/1987 | European Pat. Off. . |
| 0221707 | 5/1987 | European Pat. Off. . |

OTHER PUBLICATIONS

*Chemical Abstracts*, Fujiwara et al., Aug. 17, 1987, vol. 107, No. 7, p. 602, #57454(h).
*Chemical Abstracts*, Traeger et al., Feb. 29, 1988, vol. 108, No. 9, 109, #73715(v).
Yin–Guang-lin et al, Acta Microbiologica Sinica, 20 (3), 246–251 (1980), English translation.
Yin–Guang-lin et al, Acta Microbiologica Sinica, 21 (2), 185 (1981).
Arzneim.-Forsch./Drug Research, 36 (1), 774–778 (1986).
Tsukada–Biotechnology and Biotechnology, vol. XIV, pp. 799–810 (1972).
Martin and Perlman, European J. Appl. Microbiol, 3, pp. 91–95 (1976).

*Primary Examiner*—Ronald W. Griffin
*Assistant Examiner*—Pamela S. Webber
*Attorney, Agent, or Firm*—George M. Gould; Bernard S. Leon; William H. Epstein

[57] ABSTRACT

Disclosed is a fermentation process for the conversion of L-sorbose to 2-keto-L-gulonic acid, which is characterized in that a mixed culture of microorganisms is used, which comprises *Gluconobacter oxydans* and *Bacillus megaterium*.

18 Claims, No Drawings

FERMENTATION PROCESS

The present invention relates to a fermentation process. i.e. to a process for producing 2-keto-L-gulonic acid by fermentation. Furthermore, the invention relates to certain microorganisms which can be used in such process.

2-Keto-L-gulonic acid is an important intermediate for the production of ascorbic acid into which it can be converted according to the well-known Reichstein method.

The fermentative production of 2-keto-L-gulonic acid from D-sorbitol or L-sorbose is known.

Thus, Japanese Patent Publication No. 40154/1976 discloses the production of 2-keto-L-gulonic acid from D-sorbitol by means of microorganisms of the genus Acetobacter, Bacterium or Pseudomonas, which microorganisms are capable of oxidizing D-sorbitol under aerobic conditions, thus producing 2-keto-L-gulonic acid. The yield of this known process is, however, rather low, namely less than 6 g/l.

According to another known process, which is disclosed in "Acta Microbiologica Sinica" 21(2), 185-191, (1981). 2-keto-L-gulonic acid can be produced from L-sorbose by means of a mixed culture of microorganisms, which comprises *Pseudomonas striata* and *Gluconobacter oxydans*, the yield being 30 g/l when starting from a concentration of 70 g/l of sorbose, and 37 g/l when starting from a concentration of 100 g/l of sorbose.

According to the present invention, it is possible to produce 2-keto-L-gulonic acid from L-sorbose at a much higher yield, namely a yield of more than 40 g/l and even more than 50 g/l, when starting from a sorbose concentration of 70 g/l, and at higher yields when starting from higher concentrations.

The instant process for producing 2-keto-L-gulonic acid by conversion of L-sorbose by means of microorganisms is characterized in that a mixed culture of microorganisms comprising *Gluconobacter oxydans* and *Bacillus megaterium* is used.

We have denominated and classified the first one of these two microorganisms as *Gluconobacter oxydans* by reference to Bergey's Manual of Determinative Bacteriology, 8th edition, 1974, and, in particular, in view of the fact that it exhibits the following characteristics:
(a) 2-Keto-L-gulonic acid is produced from sorbose,
(b) ethanol is oxidized to acetic acid,
(c) D-glucose is oxidized to D-gluconic acid and 2-keto-D-gluconic acid,
(d) ketogenesis of polyalcohols,
(e) pellicle and ring growth in mannitol broth (24 hrs cultivation) at PH 4 and 5, and pellicle growth in glucose broth at pH 4.5.

In addition to the above, it exhibits the following properties:
(f) glycerol is not substantially oxidized to dihydrooxyacetone.
(g) 2-keto-D-glucaric acid is produced from sorbitol and glucaric acid, but not from glucose fructose, gluconic acid, mannitol or 2-keto-D-gluconic acid,
(h) polymorphic, apparently no flagella,
(i) brown pigment is produced from fructose,
(j) good growth when co-cultured in the presence of *Bacillus megaterium* or a cell extract thereof,
(k) streptomycin sensitive.

The second one of these two microorganisms was classified in view of the fact that it exhibits morphological, physiological cultural and other characteristics typical for *Bacillus megaterium*.

Any strains belonging to the species *Gluconobacter oxydans* on the one hand and *Bacillus megaterium* on the other hand, isolated from natural sources or obtained from publicly available collections may be useful for being employed for the instant purpose, provided they are able, in the form of a mixed culture, to convert L-sorbose to 2-keto-L-gulonic acid with a satisfying yield, i.e. a yield of more than 40 g/l, particularly of at least 50 g/l and more particularly of at least 80 g/l.

A preferred mixed culture for use in the instant process for producing 2-keto-L-gulonic acid is culture No. 2980 or a functionally equivalent culture or a subculture, mutant or variant thereof. Culture No. 2980 was deposited under DSM No. 4027 at the Deutsche Sammlung von Mikroorganismen in Göttingen on Mar. 17, 1987. Note: The present address of Deutsche Sammlung von Mikroorganismen is: Mascheroder Weg 1b, D-3300 Braunschweig, Federal Republic of Germany.

This mixed culture is composed of a *Gluconobacter oxydans* strain exhibiting the characteristics set forth under (a) to (k) above, and a *Bacillus megaterium* strain.

A specific and preferred *Gluconobacter oxydans* strain (internal designation of Academia Sinica=AS. 1.945) has been deposited at the Center for General Microbiological Culture Collection, Institute of Microbiology, Zhong Guan Cun, Beijing, China, under the designation CGMCC No. 0119 on Feb. 7, 1987. A subculture of this strain has been deposited at the Deutsche Sammlung von Mikroorganismen in Göttingen under DSM No. 4025 on Mar. 17, 1987.

A specific and preferred *Bacillus megaterium* strain (internal designation of Academia Sinica AS. 1.1484) has been deposited at the Center for Central Microbiological Culture Collection, Institute of Microbiology, Zhong Guan Cun, Beijing, China, under the designation CGMCC No. 0120 on Feb. 7, 1987. A subculture of this strain has been deposited at the Deutsche Sammlung von Mikroorganismen in Göttingen under DSM No. 4026 on Mar. 17, 1987.

The cells of both the *Gluconobacter oxydans* strain and the *Bacillus megaterium* strain are rod-shaped with rounded ends. The diameter of a cell of the *Gluconobacter oxydans* strain is, on the average about 0.3–0.6 μm, its length about 0.9–1.6 μm, mainly 1–1.5 μm. The diameter of a cell of the *Bacillus megaterium* strain is, on the average, about 1 μm–1.5 μm and its length about 2.0–5.0, mainly 4 μm. The two strain types can be easily differentiated by the above dimensions.

The quantative ratio of Bacillus colonies to Gluconobacter colonies at the beginning of the fermentation process is not critical. This ratio may e.g. be in the range between 1:10 and 1:300 (Bacillus:Gluconobacter). This ratio adjusts itself automatically, in the course of the fermentation process, to an optimal value.

The production of 2-keto-L-gulonic acid in accordance with the present invention is effected by cultivating the mixed microorganism culture referred to above in a medium containing L-sorbose as well as appropriate nutrients. Alternatively, the instant process may be carried out by culturing the mixed microorganisms referred to above and, thereafter, bringing the whole cells or a cell-free extract collected from the culture into contact with L-sorbose.

Where the mixed microorganisms are cultured in a medium containing L-sorbose as well as appropriate nutrients, the microorganisms are conveniently cultured in an aqueous medium under aerobic conditions.

The instant fermentation process may be carried out at a pH between about 5 and 8, preferably between about 6 and 8.

A preferred temperature range for carrying out the instant fermentation process is between about 25° and 35° C. More preferably, the instant fermentation process is carried out at 30°±1° C.

While the fermentation period may vary, depending on pH, temperature and nutrient medium used, usually ½ to 10 days will bring about favourable results.

The concentration of the L-sorbose substrate used as starting material in the instant process may vary between about 20 and 200 g/l, preferably between about 50 and about 100 g/l.

The culture medium used in the instant fermentation process usually contains such nutrients for the microorganisms as assimilable carbon sources, digestible nitrogen sources and inorganic substances, vitamins, trace elements and other growth promoting factors. In addition to the L-sorbose used as starting material in the instant process, other substances which are carbon sources may also be added, such as glycerol, glucose, mannitol, fructose, D-arabitol and the like.

Various organic or inorganic substances may be used as nitrogen sources in the instant process, such as yeast-extract, meat-extract, peptone, casein, corn-steep liquor, urea, amino acids, nitrates, ammonium salts and the like. As inorganic substances, magnesium sulfate, potassium phosphate, ferrous and ferric chlorides, calcium carbonate and the like may be used.

In the case, where pregrown whole cells collected from the culture, are used, the cultivation of the microorganisms is carried out under the same or similar conditions as described above. These whole cells are used in an aqueous medium under aerobic conditions, no additional nutrients (in addition to the L-sorbose used as starting material) are necessary.

In case where cell-free extracts from the culture are used, these extracts are added to the substrate in an aqueous medium and are used in the conversion of L-sorbose to 2-keto-L-gulonic acid under aerobic conditions in a manner similar to that set forth above, no additional nutrients being necessary also in this case.

According to the present process it is possible to produce 2-keto-L-gulonic acid in a yield of at least 40 g/l, preferably at least 50 g/l, most preferably at least 80 g/l.

The 2-keto-L-gulonic acid obtained according to the present process can be isolated from the reaction mixture, e.g. by the formation of a salt or by using differences in properties between the product and the surrounding impurities, such as solubility, absorbability and distribution coefficient between the solvents. Adsorption, e.g. on ion exchange resins constitutes a convenient means for isolating the product. The thus obtained product may further be purified in a conventional manner, e.g. by recrystallization or chromatography.

Alternatively, the reaction mixture can be used directly for conversion to L-ascorbic acid by esterification, followed by enolization and lactonization.

The present invention also relates to a mixed microorganism culture which can be used in the above process and which is characterized in that it comprises microorganisms of the species *Gluconobacter oxydans* and *Bacillus megaterium*.

For being useful in the above process, it is necessary that the above species are used in the form of a mixed culture, rather than individually.

A preferred mixed microorganism culture according to the instant invention is the culture No. 2980 or a functionally equivalent culture or a sub-culture, mutant or variant thereof. Culture No. 2980 was deposited under DSM No. 4027 at the Deutsche Sammlung von Mikroorganismen in Göttingen on Mar. 17, 1987.

The mixed microorganism culture according to the instant invention is characterized by the ability to produce 2-keto-L-gulonic acid from L-sorbose in a yield of at least 40 g/l, preferably at least 50 g/l, most preferably at least 80 g/l.

Thus, the term "functionally equivalent", when used in connection with other cultures, such as sub-cultures, mutants or variants of the culture No. 2980 (DSM No. 4027) refers to cultures which are able to produce 2-keto-L-gulonic acid from L-sorbose in a yield of more than 40 g/l particularly of at least 50 g/l, and more particularly of at least 80 g/l.

The present invention also relates to the individual components of the mixed microorganism culture i.e. to *Gluconobacter oxydans* cultures on the one hand and *Bacillus megaterium* cultures on the other hand, which, in combination, are able to meet the requirements set forth above for the mixed cultures, i.e. to convert L-sorbose to 2-keto-L-gulonic acid with a yield of more than 40 g/l, particularly of at least 50 g/l and more particularly of at least 80 g/l.

Representatives of such cultures are:

1. *Gluconobacter oxydans* culture AS. 1.945 (internal designation by Academia Sinica), deposited at the Center for General Microbiological Culture Collection, Institute of Microbiology, Zhong Guan Cun, Beijing, China, under the designation CGMCC No. 0119 on Feb. 7, 1987, a subculture of which was deposited at the Deutsche Sammlung von Mikroorganismen in Göttingen under DSM No. 4025 on Mar. 17, 1987.
2. *Bacillus megaterium* culture AS. 1.1484 (internal designation by Academia Sinica), deposited at the Center for General Microbiological Culture Collection, Institute of Microbiology, Zhong Guan Cun, Beijing, China, under the designation CGMCC No. 0120 on Feb. 7, 1987, a subculture of which was deposited at the Deutsche Sammlung von Mikroorganismen in Göttingen under DSM No. 4026 on Mar. 17, 1987.

Further representatives of such cultures are functionally equivalent cultures, such as sub-cultures, mutants and variants thereof.

Mutants can be derived from the parent strains by conventional methods, e.g. irradiation with u.v., X- and gamma rays or by treatment with appropriate mutagens.

The present invention is illustrated by the following Examples:

EXAMPLE 1

Fermentation in a 15 l laboratory fermentor

The mixed culture of *Gluconobacter oxydans* and *Bacillus megaterium* was streaked out on an agar petri dish containing the ingredients of the seed culture medium (below) with 2% agar.

After 4 days of incubation at 30° C. a cell suspension was made on the agar surface and used to inoculate 4 shake flasks of 2 l, each containing 400 ml of the following medium:

| | |
|---|---|
| 0.3% Yeast Extract | 0.02% MgSO$_4$.7H$_2$O |
| 0.3% Beef Extract | 0.1% Urea after sterilisation |
| 0.3% Cornsteep Liquor | 0.1% CaCO$_3$ pH 6.5 |
| 1.0% Peptone | 2.0% L-Sorbose |
| 0.1% KH$_2$PO$_4$ | add to form 1 liter with H$_2$O deionized. |

After incubation at 30° C. for 21 hours using 200 RPM the flasks were pooled. 1.4 l of these pooled broths were used to inoculate a jar fermenter containing 9 l medium with the following composition.

| | |
|---|---|
| 1% | Cornsteep Liquor |
| 0.1% | KH$_2$PO$_4$ |
| 0.01% | MgSO$_4$ 7H$_2$O |
| 0.5% | CaCO$_3$ |
| 8% | L-Sorbose |
| 1.5% | Urea |
| | add to form 1 liter with deionised H$_2$O |

After sterilization the pH is in the range of 7.6–8.0.

The aeration during the fermentation was set to 1 vvm; the agitation to 500 RPM: the temperature to 30° C. After 46 hours the L-sorbose concentration of originally 70 g/l (after inoculation) had reached zero, whereas the 2-KGA concentration reached 60 g/l.

When starting with a higher L-sorbose concentration, higher yields can be obtained.

EXAMPLE 2

The procedure of Example 1 is modified by using a production medium of the following composition, aeration speed of 0.5 vvm, agitation 800 r.p.m., at pH=7.0 (controlled with Na$_2$CO$_3$) in a 3 l (working volume 2 l) jar fermenter at 30° C.:

| | |
|---|---|
| 12.0% | L-Sorbose |
| 1.85% | Cornsteep liquor |
| 0.0086% | Mg SO$_4$.7 H$_2$O |
| 0.086% | KH$_2$ PO$_4$ |
| 0.086% | Urea |
| 0.15% | Antifoam agent CA-115 |

After 50 hours the L-sorbose concentration of originally 110 g/l was 20 g/l, whereas the 2-KGA concentration was 81 g/l.

We claim:

1. A process for converting L-sorbose to 2-Keto-L-gulonic acid comprising producing L-sorbose 2-keto-L-gulonic acid by cultivating a mixed microorganism culture system containing *Gluconobacter oxydans* and *Bacillus megaterium*, or whole cells or a cell free extract produced from said mixed culture system in a nutrient medium containing L-sorbose to convert the L-sorbose in said medium to 2-keto-L-gulonic acid, said culture system having the identifying characteristics of culture system 2980, Deutsche Sammlung Von Microorganismen No. 4027, said culture system being capable of converting L-sorbose to 2-keto-L-gulonic acid in a yield of greater than about 40g/l.

2. The process of claim 1 wherein conversion is carried out by cultivating said microorganism culture system in said medium containing L-sorbose.

3. The process of claim 2 wherein said *Gluconobacter oxydans* in said culture system has the identifying characteristics of DSM No. 4025.

4. The process of claim 3 wherein said *Bacillus megaterium* in said culture system has the identifying characteristics of DSM No. 4026.

5. The process of claim 4 wherein said medium has an L-sorbose concentration of from about 20 g/liter to about 200 g/liter.

6. The process of claim 5 wherein said fermentation is carried out at a pH of from about 5 to 8 at a temperature of from about 25° C. to about 35° C.

7. The process of claim 1 wherein said conversion is carried out by cultivating with whole cells or with the cell free extract in said medium containing L-sorbose.

8. The process of claim 7 wherein said *Gluconobacter oxydans* in said culture system has the identifying characteristics of DSM No. 4025.

9. The process of claim 8 wherein said *Bacillus megaterium* in said culture system has the identifying characteristics of DSM No. 4026.

10. The process of claim 9 wherein said medium has an L-sorbose concentration of from about 20 g/liter to about 200 g/liter.

11. The process of claim 10 wherein said fermentation is carried out at a pH of from about 5 to 8 at a temperature of from about 25° C. to about 35° C.

12. A microorganism culture system comprising a mixture formed from a biologically pure culture of microorganism of the species *Gluconobacter oxydans* and a biologically pure culture of a microorganism of the species *Bacillus megaterium*, said culture system having the identifying characteristics of DSM No. 4027 and being capable of converting L-sorbose to 2-keto-L-gulonic acid in a yield of greater than 40 g/l.

13. The culture system of claim 12 wherein said *Gluconobacter oxydans* in said culture system has the identifying characteristics of DSM No. 4025.

14. The culture system of claim 12 wherein said *Bacillus megaterium* in said culture system has the identifying characteristics of DSM No. 4026.

15. A biologically pure culture of the microorganism of *Gluconobacter oxydans* with the identifying characteristics of DSM No. 4025.

16. The biologically pure culture of claim 15 wherein said microorganism is capable in combination with a *Bacillus megaterium* strain, having the identifying characteristics of DSM No. 4026 of converting L-sorbose to 2-keto-L-gulonic acid in a yield of at least 40 g/l.

17. A biologically pure culture of the microorganism *Bacillus megaterium* with the identifying characteristics of DSM No. 4026.

18. The biologically pure culture of claim 17 wherein said microorganism is capable in a mixed culture system with a *Gluconobacter oxydans* strain, having the identifying characteristics of DSM No. 4025, of converting in a fermentation medium L-sorbose to 2-keto-L-gulonic acid in yield of at least 40 g/l.

* * * * *